United States Patent [19]

Steinle et al.

[11] Patent Number: 4,858,461
[45] Date of Patent: Aug. 22, 1989

[54] PERMEATION CELL GAS DETECTOR

[75] Inventors: Shelton Steinle, Richmond, Calif.; John P. Sturtz, Hudson, Ohio; Yogeshwar Dayal; Lealon C. Wimpee, both of San Jose, Calif.

[73] Assignee: General Electric Company, San Jose, Calif.

[21] Appl. No.: 102,441

[22] Filed: Sep. 29, 1987

[51] Int. Cl.$^4$ .......................................... G01N 31/00
[52] U.S. Cl. ...................................................... 73/23
[58] Field of Search ................. 73/23, 29, 863.23, 19; 422/83, 88; 55/16; 340/632

[56] References Cited

U.S. PATENT DOCUMENTS

| | | | |
|---|---|---|---|
| 2,671,337 | 3/1954 | Hulsberg | 73/23 |
| 3,431,771 | 3/1969 | Tsien | 73/23 |
| 3,545,931 | 12/1970 | McKinley, Jr. | |
| 3,604,246 | 9/1971 | Toren | 73/19 |
| 3,681,026 | 8/1972 | Holden | 73/23 |
| 3,718,434 | 2/1973 | Pierce | 73/23 |
| 3,864,628 | 2/1975 | Klass et al. | 73/23 |
| 3,926,561 | 12/1975 | Lucero | |
| 4,402,211 | 9/1983 | Sugawara et al. | 73/19 |

Primary Examiner—Hezron E. Williams
Attorney, Agent, or Firm—Robert R. Schroeder

[57] ABSTRACT

Assuming knowledge of the number and species of gases present within an enclosed environment such as the atmosphere of a containment vessel of a nuclear plant, an apparatus and process for receiving a gas sample from said atmosphere and measuring the percentages of the various known number and species of gases present is disclosed. Assuming N number of gas species present, N-1 discrete chambers are utilized. Each chamber confines the sample gas, includes a discrete permeation cell having an internal volume isolated from the rest of the chamber by a permeable membrane, and has a pressure sensor for measuring the pressure within the permeation cell resulting from gas permeating through the permeable membrane. Each chamber is isothermal and maintained at its own discrete temperature. Sample gas is introduced into each chamber and allowed to come to equilibrium with the temperature of the chamber. When thermal equilibrium is attained, the permeation cell in each chamber is evacuated by a vacuum pump. Thereafter, gas permeation through each membrane occurs for a given and measured period of time. This period of time is chosen so that the pressure buildup resulting from gas permeating into the cell is but a small fraction of the total sample gas pressure in each chamber. Thereafter, the permeation rates for each cell at each cell's temperature together with the total sample gas pressure are solved in a simultaneous equation format to determine the percentage of each of the N gas species present.

9 Claims, 4 Drawing Sheets

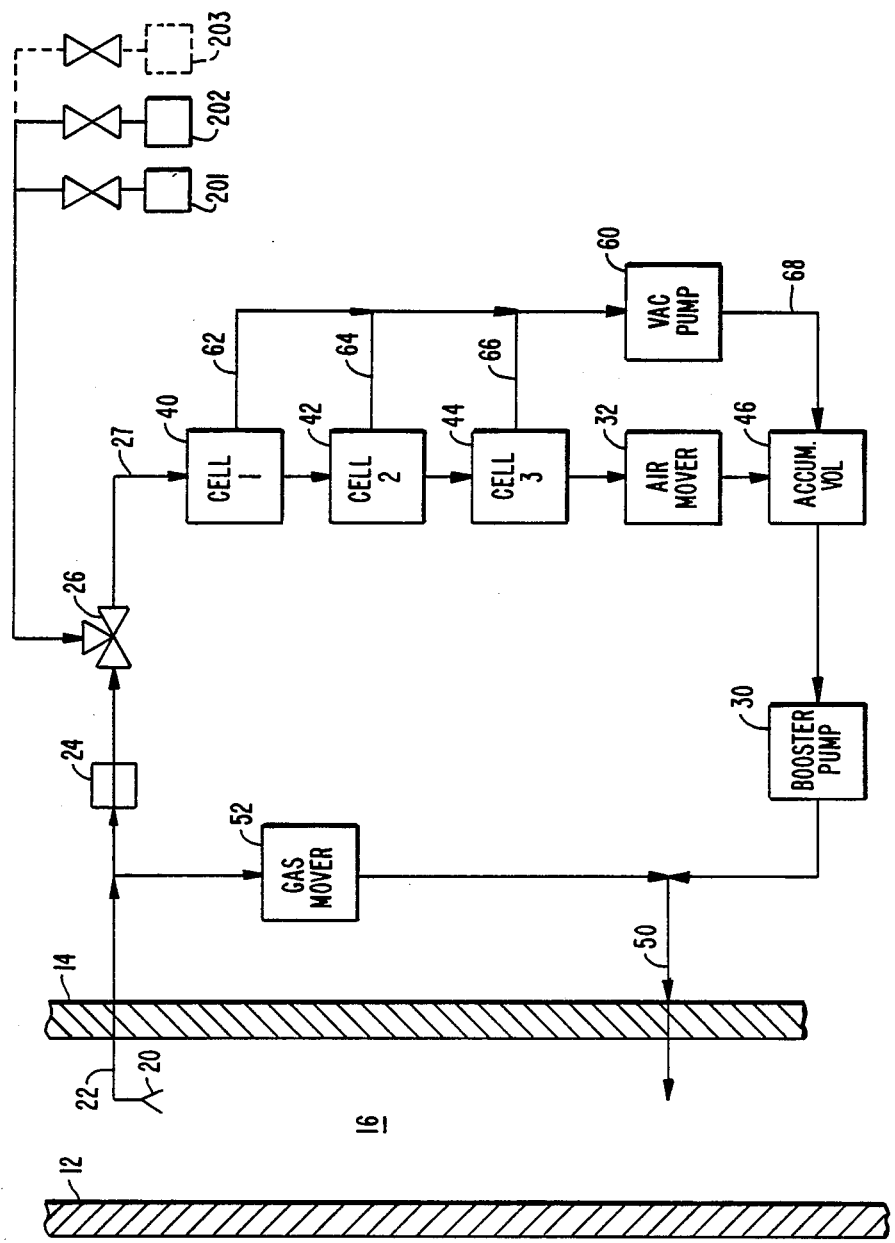
FIG._1.

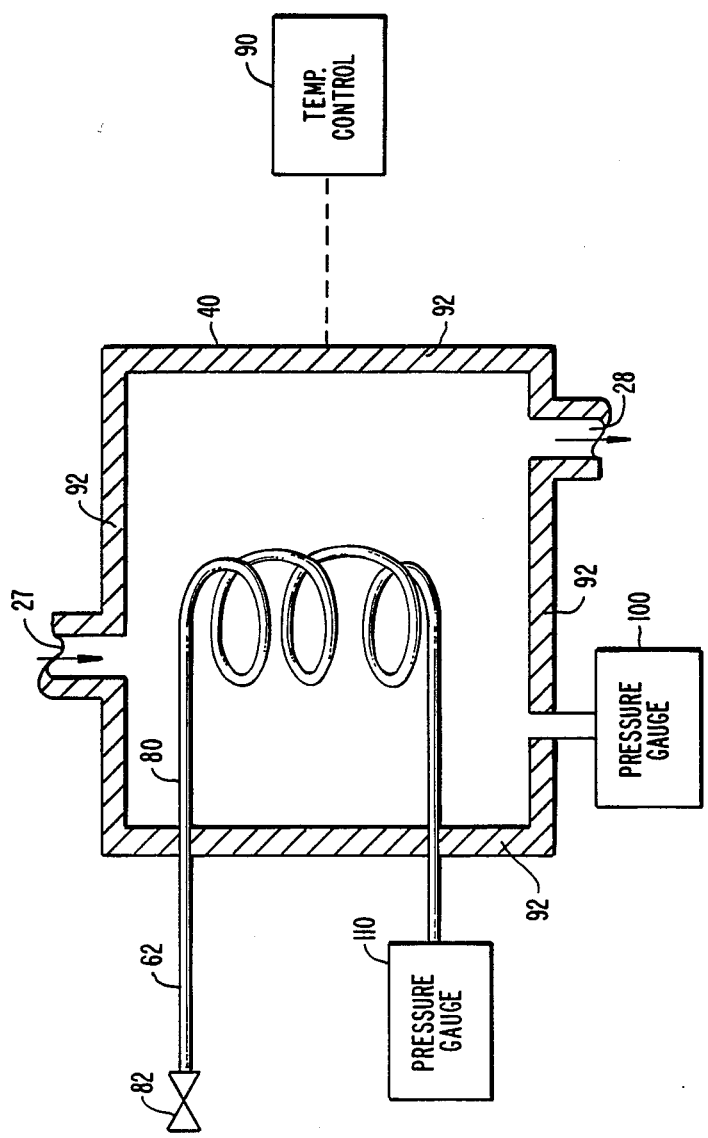
FIG._2.

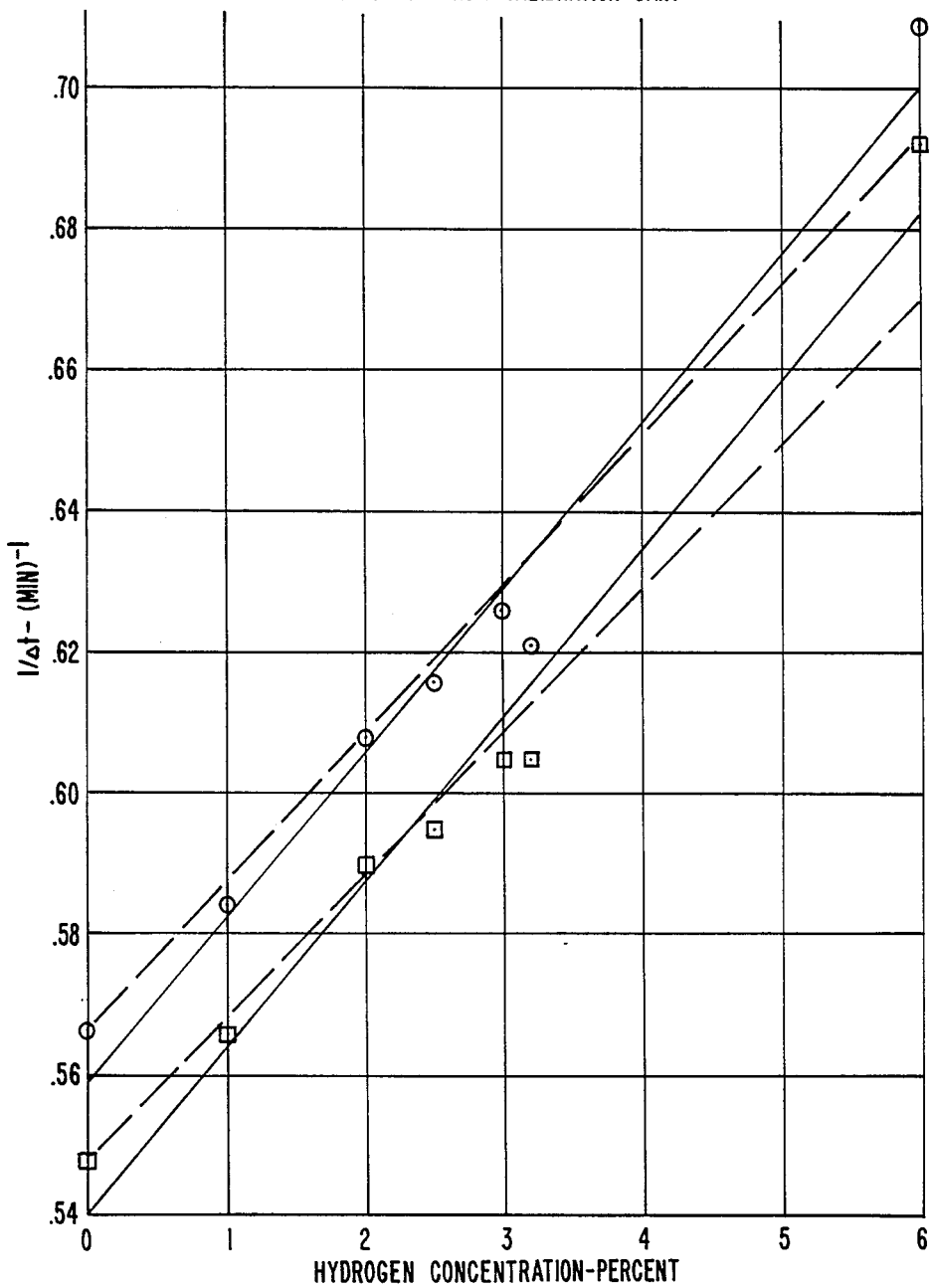
FIG._3.

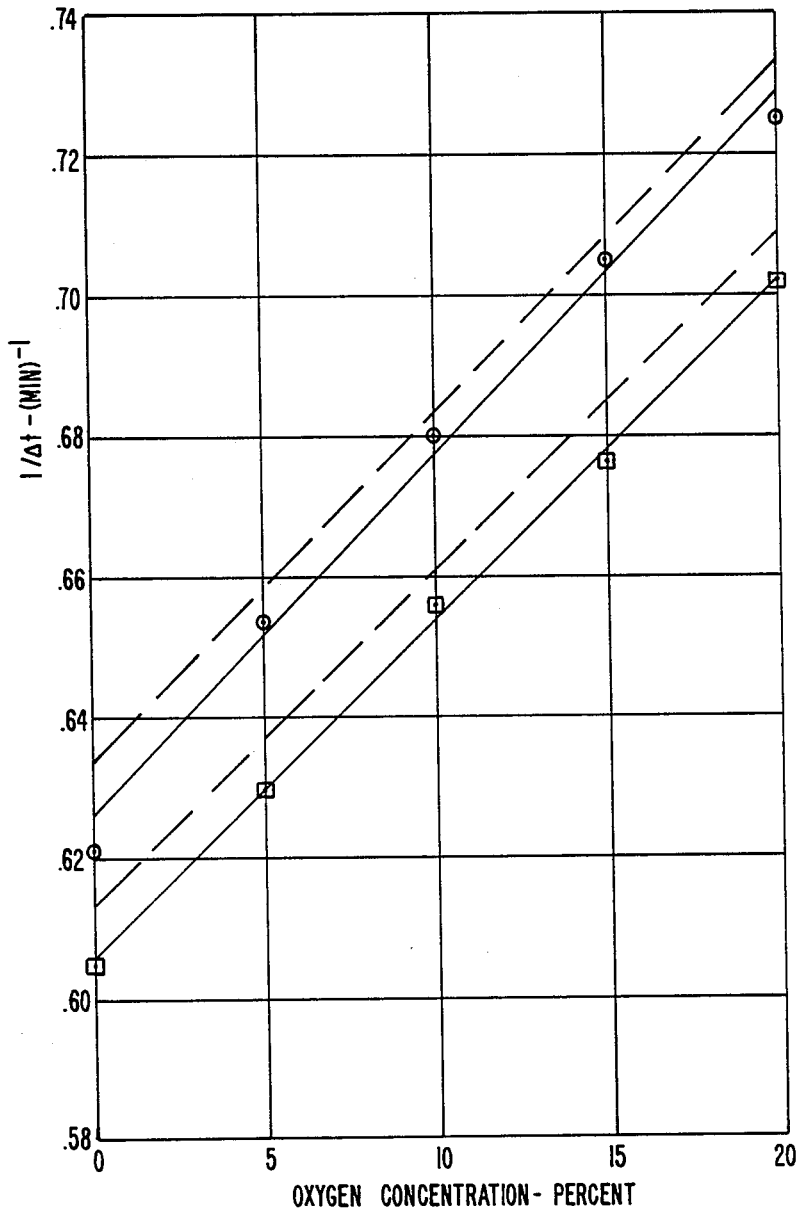
FIG._4.

PERMEATION CELL GAS DETECTOR

BACKGROUND OF THE INVENTION

This invention relates to the monitoring of gases. More specifically an apparatus and process for receiving a gas sample and measuring the percentages of various known constituent gas species is disclosed. A possible application includes potentially explosive environments such as the atmosphere within a nuclear containment vessel.

SUMMARY OF THE PRIOR ART

It is known that a gas will permeate across membranes. In one relevant embodiment it is desired to introduce a trace gas into a bulk gas. The trace gas is contained on one side of a permeable membrane and the membrane is heated, allowing the trace gas to pass through the membrane into the bulk gas on the other side of the membrane. Permeation occurs at a rate dependent upon temperature and configuration of the membrane. In general, the permeation rate is different for each gas species, for each membrane material, and for each temperature. Gas species permeate independently when present in mixtures. By calibrating the membrane system, an accurate flow rate of the trace gas to the bulk gas is obtained.

In McKinley, Jr. U.S. Pat. No. 3,545,931 ammonia is permeated or diffused across a membrane. Thereafter it is dissociated into its hydrogen and nitrogen components. The free hydrogen is measured by conventional means.

In Lucerno, U.S. Pat. No. 3,926,561, permeation of a trace gas occurs by permeation across a membrane to a carrier gas. Thereafter, the trace gas components in the carrier gas are measured. These measurements include maxima or "plateaus". When the plateaus are compared one against another, the relative proportions of the contained constituents can be determined.

Statement of the Problem

Measurements of gases in potentially explosive environments are required. For example, the atmosphere within the containment vessel of a nuclear power plant can be such an environment. Associated with one type of nuclear accident is the dissociation of hydrogen from the water within the nuclear reactor. Where hydrogen in substantial quantities (above 5%) is within the atmosphere of the containment vessel, a potentially explosive condition can exist.

There is a need to monitor the atmosphere within the containment vessel. Unfortunately, this atmosphere is hostile. It is not accessible, is subject to contamination, and in the event of an accident can become radioactive. What is needed is a gas detector which can never be a source of ignition and which can withstand the hazards of the environment including radioactivity.

In an effort to neutralize the region between the reactor pressure vessel and the containment vessel ("containment atmosphere"), it is known to flood this area with a chemically inert gas to prevent possible explosion. For example, a nitrogen gas blanket has been used. Such "inserting," however, is expensive and can be dangerous. The blanketing gas can escape and cause a hazard.

Conventional gas sensors will not function adequately in this environment.

Conventional gas spectrometers are too delicate. These instruments have difficulty withstanding the heat in the containment vessel atmosphere environment. Moreover, they can be rendered inoperative by the radiation that is encountered.

Hydrogen sensors working on the gettering principle are subject to surface contamination which adversely affects the performance. That is to say, small amounts of impure gases can be adsorbed on the gettering surfaces of such instruments. The measurement of hydrogen content by such instruments is severely compromised by surface adsorbed contaminating gases.

Heated filament type sensors present an undesirable ignition source.

SUMMARY OF THE INVENTION

The apparatus and procedure described herein provides a method of sampling and determining the percentages of gas species present in the atmosphere within a contained region, such as the atmosphere within the containment of a nuclear power plant. Use of this equipment requires that the number and species of the major gas constituents in the sample be known (excluding trace gas components). Assuming that the atmosphere to be sampled and analyzed contains N constituent gas species, N items of data are required. To obtain these data, N-1 discrete measuring chambers and the total system pressure preferably are used. Each chamber contains a gas sample inlet port, a gas sample outlet port, and a means of maintaining the chamber at a constant temperature. A sealed permeation membrane, or cell is contained within each chamber; attached to this cell is a pressure gauge to measure the cell's internal pressure and a means of exhausting the interior of the cell to vacuum. The several cells may be constructed of the same membrane material and operated at differing temperatures, may be constructed of different membrane materials and operated at the same temperature, or a combination thereof so that different temperature coefficients for the membrane permeation rates are obtained in all cases. For the case of where different membrane materials are operated at the same temperature, it is possible for all cells to be contained within a single isothermal chamber. The permeation characteristics for each cell for each of the gas species present are predetermined. The inlets of the several chambers are connected such that the sample gas pressure ("total gas pressure") in all chambers is the same, and a means is provided for measuring this total gas pressure.

The system is operated as follows: The several chambers are set at their prescribed temperatures. Sample gas is admitted to the chambers and allowed to come to thermal equilibrium with the chamber. The interior of each permeation cell is then evacuated by the vacuum pump. Sample gas is allowed to permeate into each cell either for a fixed and measured period of time or alternately, until a fixed and measured pressure increase is produced. The sampling time is chosen so that the gas permeation across the membrane is substantially linear with time and the gas pressure buildup within the cell is a small fraction of the total gas pressure. At the end of the permeation time, the gas pressure within each cell and the total gas pressure are measured. The N-1 cell pressures and the total pressure are input as variables into an array of N equations, and the solution of these N equations allows calculation of the partial pressures of each of the N gas species in the sample.

Other Objects and Advantages

An object of this invention is to use permeation across a gas permeable membrane for gas constituent measurement of a plurality of mixed gas species. Typically, one side of the membrane is evacuated. The other side of the membrane is flooded with the sample gas at a constant temperature. After evacuation, gas is allowed to permeate through the membrane for a given period of time. The temperature, geometry, and material of each membrane determines the rate of gas permeation through the membrane into the cell for each gas species. Assuming that the total pressure accumulated within the cell is but a small fraction of the total pressure of the sample gas within the chamber, a substantially linear permeation rate of gas will occur with time. Knowing the permeation characteristics and permeation times for each cell for each gas species, these linear rates of permeation (hence pressure build-up within the cells) are used as inputs to an array of simultaneous equations whose solution permits calculation of the partial pressures of the gas species present in the sample.

An advantage of this apparatus and method is that the disclosed gas analyzer is rugged. It has no moving parts, no delicate filaments, no surfaces which are readily contaminated. The apparatus itself does not and cannot constitute an ignition source.

An additional advantage is that the device is inert with respect to the gases being sampled. No chemical reactions occur. There are no catalytic reactions on sensitive surfaces utilizing the gettering principle.

A further advantage is that the sample flow rate through the gas analyzer is not critical. Moreover, the method and apparatus is operable over a wide range of ambient temperatures.

A further advantage is that the gas analyzer can, from time to time, be calibrated for each of the species being detected. Thus, aging of the membrane does not degrade the performance of the apparatus and method. Further, the gas analyzer is not subject to surface contamination.

Further, the device is operated utilizing simple, rugged electronics in the hazardous zone with all sophisticated equipment mounted remotely. All that is required is timed valve operation and the measurement of pressure. The disclosed analyzer additionally has moderate radiation tolerance. Operability can be expected even where contained accidents occur in a nuclear reactor.

BRIEF DESCRIPTION OF THE DRAWINGS

Other objects, features and advantages of this invention will become more apparent after referring to the following specification and attached drawings in which:

FIG. 1 is a schematic of the gas sampler including three chambers for monitoring four unknown gas components:

FIG. 2 is a typical embodiment of one of the chambers of FIG. 1:

FIG. 3 illustrates measurement of hydrogen concentration: and

FIG. 4 illustrates measurement of oxygen concentration.

DESCRIPTION OF THE PREFERRED EMBODIMENTS

Referring to FIG. 1, a reactor pressure vessel wall 12 is illustrated surrounded by a containment vessel wall 14 defining a containment vessel interstice 16 therebetween. It will be understood that reactor vessel wall 12 contains a nuclear reactor core (not shown). Likewise containment vessel wall 14 completely surrounds the reactor vessel wall 12. In the event of a nuclear accident, it is the intent that containment wall 14 will confine the casualty.

The usual and normal state of the atmosphere 16 within the nuclear reactor is that it is confined (to prevent possible escape of radioactivity), hot and in intimate contact with the reactor vessel.

Of numerous possible nuclear casualties, a casualty which dissociates hydrogen from water and causes accumulation of hydrogen within atmosphere 16 is known. Clearly, the explosive accumulation of hydrogen in the atmosphere 16 must be avoided. Such avoidance must occur both during normal operation and during casualty which can release radioactive materials.

Having set forth the typical environment in which this gas measurement device can reside, the measurement system will now be described.

The measurement system includes a filter 20 attached to a sample gas inlet 22. Gas mover (pump) 52 pulls a sample of the atmosphere 16 through the inlet 22; a portion of this sample is routed to a condenser 24 where water vapor is removed or the water vapor and the water concentration stabilized, through a three-way valve 26 to the inlet to the first analyzing chamber 40. Booster pump 30 and air mover 32 cause the sample gas to flow through the first chamber 40, the second chamber 42, and the third chamber 44. Excess sample gas passes to accumulator volume 46, from which booster pump 30 circulates it back to the containment atmosphere 16 via outlet line 50.

The reader will understand that water vapor can be considered as a constituent gas. Alternately, the whole system can be offset by a constantly present amount of water vapor, the exact measurement of this water vapor being ignored.

Continual circulation and sampling of the containment atmosphere can be provided by a gas mover 52. Thus, upon actuation (opening) of valve 26, random and rapid sampling of the atmosphere 16 is assured.

A vacuum pump 60 communicates through lines 62, 64, 66 to each of the respective permeation cells contained within chambers 40, 42, 44. Output of the vacuum pump 60 at line 68 passes to the accumulator volume 46, the booster pump 30, the outlet line 50 and back to the containment atmosphere 16.

Having set forth the overall piping of the system, a typical chamber 40, 42, 44 will be discussed with reference to FIG. 2. Referring to FIG. 2, chamber 42 is illustrated.

Chamber 42 includes sample inlet 27 and sample outlet 28. A helical tube ("cell") of permeation tubing 80 is contained within cell 42. Cell 80 is hollow in its interior. Its walls have sufficient rigidity to withstand a substantial vacuum. Thus, when a vacuum is drawn on the interior of cell 80 through line 62, with control at a valve 82, collapse of the cell does not occur.

Housing 42 is provided with a temperature control 90 and insulated walls 92. It will be understood that the chamber interior is controlled as to its temperature.

It is required for the practice of this invention that the gas within the chamber be maintained at a known and constant temperature. In the embodiment in which all permeation cells are made of the same permeable material, each chamber must be operated at a temperature different from each other chamber. In the embodiment in which all permeation cells are made of different materials, the chambers may be operated at the same or different temperatures. This is necessary to produce the differing permeation rates for the several gas species essential to establishing the array of equations whose solution calculates the partial pressures of the gas species in the sample.

Referring to FIG. 1, operation will include activating gas mover 52, air mover 32, and booster pump 30 and opening three-way valve 26 so as to pass a fresh sample of containment gas 16 into the respective chambers 40, 42, 44. Thereafter, booster pump 30 and air mover 32 will be shut down and the chambers will thermally equilibrate with the sample gas in each chamber equilibrating to that chamber's temperature.

When thermal equilibration has occurred each of the chambers 40, 42, and 44, will have the equivalent of valve 82 in chamber 42 opened. At the same time, vacuum pump 60 will draw a vacuum on the permeation cell 80 (see FIG. 1 and FIG. 2).

Once a vacuum has been drawn, vacuum pump 60 is shut down and valves 82 closed. Thereafter, measurement of pressure accumulated in the cells will occur after a discrete and measured period of time. The pressure in each cell will result from the cumulative permeation of all the gases through that cell's membrane at that cell's particular temperature for each chamber 40, 42, 44.

It will be noted that the system includes a pressure gauge 100. This pressure gauge 100 measures the total pressure of the atmosphere surrounding each cell. This measurement of total gas pressure is required. Since all chambers are at the same pressure, only one such gauge is required.

Kin-Tek Laboratories of Texas City, Tex., manufactures and markets a line of permeation membranes sold under the trademark "Trace Source." These membranes are used for introducing controlled quantities of specific trace gases into bulk sample gas or gas mixture volumes (see prior art).

The cell 80 is made from the material of these permeation membranes, although others may be used.

In general, the permeation rate is chosen to be different for each gas, each membrane material, each membrane configuration, and each temperature. The present invention operates by calibrating the membrane system. Hence an accurate known permeation rate for each of the constituent gases in the sample is obtained.

In the monitoring of a containment atmosphere volume, the principal gases of interest are water vapor, hydrogen, nitrogen and oxygen. Each of these gases will have a significantly different permeation rate for each of the membranes. Once the vacuum has been drawn within the cell 80, the inside of the cell 80 will be at vacuum while the outside is exposed to gases of the sample at substantially atmospheric pressure within the chamber. The pressure buildup in the low pressure side of the cell measured by pressure gauge 110 will accrue from the atmosphere inside the containment volume. By utilizing different chamber temperatures and/or cell materials, the following matrix can be produced to determine the partial pressure of the gas constituents, (hydrogen, nitrogen, water vapor and oxygen) present.

$$K_{1,1}P_1 + K_{1,2}P_2 + \ldots K_{1,n}P_n = P_{c1} \quad \text{(cell 1)} \quad (T_1) \quad (1)$$
$$K_{2,1}P_1 + K_{2,2}P_2 + \ldots K_{2,n}P_n = P_{c2} \quad \text{(cell 2)} \quad (T_2)$$
$$K_{n-1,1}P_1 + K_{n-1,2}P_2 + \ldots K_{n-1,n}P_n = P_{c(n-1)} \quad \text{(cell N - 1)} \quad (T_{n-1})$$
$$P_1 + P_2 + \ldots P_n = P_{Total}$$

where the K's are the permeation coefficients for the gas constituents at the appropriate membrane temperatures the P's are the partial pressures of the gas constituents and the $P_c$'s are the pressures measured within the cells. For example, the first equation could be written for cell 1 at temperature $T_1$ in which $K_{1,1}$ is the permeation coefficient for hydrogen and $P_1$ the partial pressure of hydrogen in the sample; $K_{1,2}$ is the permeation coefficient for oxygen and $P_2$ the partial pressure of oxygen: $K_{1,3}$ is the permeation coefficient for nitrogen and $P_3$ the partial pressure of nitrogen, etc. Thus, if n gas constituents must be measured, it is necessary to have n-1 membranes, plus a measure of the total gas pressure.

In the example, the measurement system requires measurement of nitrogen, hydrogen, oxygen, and water vapor. If the water vapor is condensed out to stabilize the gas, and is measured separately, the measurement of nitrogen, hydrogen and oxygen would require only two membranes and total system pressure. If the oxygen content is measured independently by other means then only one membrane is required. For multiple membrane sensors, the different K values can be obtained either by operating the same permeation membrane material at different temperatures or by different materials at the same temperature.

We have here illustrated a preferred measurement chamber array including three chambers.

An approximate solution, valid for short times when the diffusion rate is nearly constant with time, is:

$$C_{1,1}P_1 + C_{1,2}P_2 + \ldots C_{1,n}P_n = \frac{dP_{c1}}{dt} \quad (T_1) \quad (2)$$
$$C_{2,1}P_1 + C_{2,2}P_2 + \ldots C_{2,n}P_n = \frac{dP_{c2}}{dt} \quad (T_2)$$
$$C_{n-1,1}P_1 + C_{n-1,2}P_2 + \ldots C_{n-1,n}P_n = \frac{dP_{c(n-1)}}{dt} \quad (T_n - 1)$$
$$\text{and } P_1 + P_2 + \ldots P_n = P_{Total}$$

where, $C_{1n}$ is a constant defining the diffusion rate of gas species n through the membrane in Chamber 1 (at temperature $T_1$) and proportional to the permeation constant $K_{1n}$; and $dP_{c1}/dt$ is the rate at which the pressure in the cell of Chamber 1 (at temperature $T_1$) is changing with time.

From a product implementation point of view, operation in the transient mode, described by equations (2) above, is preferable to operation in the steady state mode (equations (1)), since the former has a much shorter measurement time, and hence can provide a read out of the gas species move quickly.

EXAMPLES

The permeation membrane (cell) tested consisted of a Teflon FEP tube having 0.060 inch O.D. x 0.015 inch wall, 1.0 pk meter long. This membrane had been calibrated for hydrogen, oxygen, and nitrogen prior to testing (see Emission Rate Data Tables 2, 3, and 4). Cell 80 was coiled and placed inside an insulated, hollow aluminum block which had heaters and a temperature controller attached to the outside. The gas mixtures were introduced into the block cavity through a flow meter, and were vented to atmosphere, thus producing a pressure outside the membrane of one atmosphere. One end of the tube was closed and the other attached to a pressure gauge, with provision for periodically evacuating the inside diameter of cell 80 by means of a Welch mechanical vacuum pump. The pressure gauge output was fed to a digital voltmeter. All measurements reported here were made with the membrane at approximately 118.4° C., the maximum temperature available for the temperature controller.

A typical data point was produced by exhausting the inside of the membrane to vacuum for 15 seconds, closing the pump valve, and observing the pressure rise as indicated by the voltmeter. The time for the pressure readout to pass from 0.500 volts to 0.800 volts was measured. The pressure gauge output also was recorded using a strip chart recorder. The time cycle for a measurement was approximately four minutes.

The first data were taken using pure nitrogen as the sample gas. For this case, the rate of pressure rise inside the membrane is (2)

$$\frac{\Delta p}{\Delta t} = C_N P_N$$

where $P_N$ is the nitrogen pressure (1.0 atmosphere) and $C_N$ contains the permeation coefficient and geometrical factors. Thus for a fixed pressure differential, $\Delta p$, (3)

$$\frac{1}{\Delta t} = K_N f_N$$

where $f_N$ is the fractional gas composition (1.00 in this case), $K_N$ contains the permeation coefficient, geometry factors and measurement units, and $\Delta t$ is the time interval for the pressure readout to pass from 0.500 volts to 0.800 volts.

During the initial test, it was found that the temperature controller produced a cyclical temperature variation of a few tenths of a degree Centigrade, with a time constant of approximately 65 minutes. This resulted in a corresponding variation the measured value of $\Delta t$. In order to compare various gas mixtures on the same basis (i.e. same membrane temperature), the corresponding maximum and minimum values of $\Delta t$ were recorded. For the case of pure nitrogen, these times were 1.828 minutes and 1.768 minutes, respectively.

Thus, from (3) above $K_N = 0.547$ (at max temp) and 0.566 (at min temp).

The next series of data were taken using nitrogen/hydrogen mixtures containing 1.0, 2.0, 2.5, 3.0, 3.2, and 6.0 percent hydrogen (balance nitrogen), the procedure being the same as that described above. These data are shown in FIG. 3. The solid line shows a linear fit to the data, using the least squares technique.

From the membrane calibration data, the ratio of the hydrogen permeation to the nitrogen permeation at 118.5° C. is 4.758. For this gas mixture $$\frac{1}{\Delta t} = K_N f_N + K_H f_H = K_N f_N + 4.758 \, K_N f_H. \quad (4)$$

Introducing the value of $K_N$ determined above and the appropriate values of $f_N$ and $f_H$ produces the broken lines shown in FIG. 3.

The final series of data were taken using nitrogen/hydrogen/oxygen mixtures containing 3.2% hydrogen: 5—, 10—, 15—, and 20% oxygen: and the balance nitrogen, the procedure again being the same as that described above. These data are shown in FIG. 4. The solid line shows a linear fit to these data.

The ratio of the oxygen permeation to the nitrogen permeation is 1.879. For this gas mixture $$\frac{1}{\Delta t} = K_N f_N + K_H f_H + K_O f_O \quad (5)$$
$$= K_N f_N + 4.758 \, K_N f_H + 1.879 \, K_N f_O$$

Introducing the appropriate $K_N$ and $f_N$, $f_H$, and $f_O$ values produces the broken lines shown in FIG. 3.

Additional membranes were irradiated at the Vallecitos cobalt-60 facility to exposures of $10^4$, $10^5$, $10^6$ Rad and returned for calibration of the hydrogen permeation rates. Results are shown in Table 1.

TABLE 1

Permeation Membrane Radiation Tolerance
Membrane Material: Teflon FEP

| Radiation Exposure | Permeability After Radiation (nl hydrogen at STP/min atm) | | | | |
|---|---|---|---|---|---|
| | 60° C. | 80° C. | 100° C. | 120° C. | 150° C. |
| 0 | 76,500 | 132,000 | 215,000 | 338,000 | 602,000 |
| $10^4$ Rad | 75,500 | 131,000 | 211,000 | 332,000 | 599,000 |
| $10^5$ Rad | 77,000 | 131,000 | 208,000 | 317,000 | 552,000 |
| $10^6$ Rad | 70,800 | 146,000 | 273,000 | 492,000 | 1,050,000 |
| $10^8$ Rad | Failed mechanically | | | | |

Note that the change in permeation rate is negligible at $10^4$ Rad, slight at $10^5$ Rad, and significant at $10^6$ Rad. At $10^8$ Rad the membrane was sufficiently brittle that it broke while removing it from the radiation capsule. The changes in permeation rate are not necessarily catastrophic, but would require more frequent recalibration of the sensor when they occurred. It is believed that the radiation contribution from beta particles in the sample gas can be reduced significantly by incorporating shielding around the membrane.

Tables 2, 3, and 4 are included herein. These tables show the permeation rates for hydrogen, oxygen, and nitrogen, respectively, through the membranes. One having skill in the art may construct this invention using this data.

TABLE 2

EMISSION RATE DATA
Trace Source ™ Series 57 Permeation Source
Permeating Fluid: Hydrogen
KTL Part No.: 57HB-300-504
Test Date: 5/1/80

| Temperature (° C.) | Emission Rate (nanoliters at S.T.P./min. atm) |
|---|---|
| 20 | |

TABLE 2-continued

EMISSION RATE DATA
Trace Source ™ Series 57 Permeation Source
Permeating Fluid: Hydrogen
KTL Part No.: 57HB-300-504
Test Date: 5/1/80

| Temperature (° C.) | Emission Rate (nanoliters at S.T.P./min. atm) |
|---|---|
| 25 | 23,693 |
| 30 | 28,395 |
| 35 | |
| 40 | 40,081 |
| 50 | 55,383 |
| 60 | 75,054 |
| 80 | 130,901 |
| 100 | 215,087 |
| 120 | 336,000 |
| 150 | 606,159 |

Minimum Recommended Operating Temperature: 25° C.
Maximum Recommended Operating Temperature: 150° C.

TABLE 3

EMISSION RATE DATA
Trace Source ™ Series 57 Permeation Source
Permeating Fluid: Oxygen
KTL Part No.: 57HB-300-504
Test Date: 5/6/80

| Temperature (° C.) | Emission Rate (nanoliters at S.T.P./min. atm) |
|---|---|
| 20 | |
| 25 | 7,319 |
| 30 | 8,906 |
| 35 | |
| 40 | 12,940 |
| 50 | 18,371 |
| 60 | 25,538 |
| 80 | 46,666 |
| 100 | 79,936 |
| 120 | 129,628 |
| 150 | 245,706 |

Minimum Recommended Operating Temperature: 25° C.
Maximum Recommended Operating Temperature: 150° C.

TABLE 4

EMISSION RATE DATA
Trace Source ™ Series 57 Permeation Source
Permeating Fluid: Nitrogen
KTL Part No.: 57HB-300-504
Test Date: 5/5/80

| Temperature (° C.) | Emission Rate (nanoliters at S.T.P./min. atm) |
|---|---|
| 20 | |
| 25 | 1,932 |
| 30 | 2,467 |
| 35 | |
| 40 | 3,927 |
| 50 | 6,076 |
| 60 | 9,156 |
| 80 | 19,394 |
| 100 | 37,903 |
| 120 | 69,195 |
| 150 | 153,405 |

Minimum Recommended Operating Temperature: 25° C.
Maximum Recommended Operating Temperature: 150° C.

It can be expected that the cell membranes will from time to time require calibration.

This calibration will be required because the cell membranes may "age" in their respective chambers. Referring back to FIG. 1, it will be seen that oxygen source 201, nitrogen source 202, and hydrogen source 203 are all shown connected to the system via three way valve 26. These sources allow these gases to be introduced for periodic calibration of the cells.

It will be appreciated that although preferred use of this device is disclosed in the containment atmosphere, the device may as well be used elsewhere.

It will be understood that for the technique described herein, we require permeation and not diffusion. Simply stated, diffusion is orders of magnitude faster than permeation and generally does not provide the accuracy required for the relatively precise measurement of gases as set forth here.

What is claimed is:

1. Apparatus for receiving a sample gas and measuring the percentages of various known number (N) and kind of gas species present within said sampling comprising:

a plurality of chambers, each chamber configured to receive and confine sample gas;

each chamber further including a discrete permeation cell having an internal volume isolated from the chamber by a permeable membrane;

each chamber including a pressure sensor for measuring the pressure within the permeation cell resulting from gases permeating through the permeable membrane;

a sensor for measuring the pressure of the gas sample surrounding the permeation cell;

means for evacuating the permeation cells; and means for measuring the pressure buildup within said cells; said apparatus including a plurality of said chambers including at least (N-1) chambers;

means for maintaining each chamber at a discrete temperature, said temperature for each chamber different than the temperature of all other chambers.

2. Apparatus according to claim 1 for receiving a sample gas and wherein said chambers include tubing defining said discrete permeation cells.

3. The apparatus of claim 1 in wherein said permeations cells have differing temperature coefficients of permeation rates.

4. A process for receiving a gas sample and measuring the percentages of various known number (N) and kind of gas species present within said sample, comprising the steps of:

providing at least (N-1) chambers, each provided chamber including a volume for isolating said sample gas and a permeation cell having an internal volume isolated from the rest of the chamber by a permeable membrane;

maintaining each chamber at its own discrete temperature for a sufficient interval of time to thermally equilibrate the gas sample to the temperature of said chamber;

evacuating the permeation cell of each said chamber;

immediately after said evacuation step measuring the pressure buildup in said permeation cell for a sufficient interval of time during which a substantially linear permeation rate of gas across said membrane exists;

measuring the total sample gas pressure in said chambers; and, determining from said measured pressures in said (N-1) cells the percentages of gases present by solving;

$$K_{1,1}P_1 + K_{1,2}P_2 + \ldots K_{1,n}P_n = \frac{dP_{c1}}{dt}(T_1) \quad (1)$$

-continued $$K_{2,1}P_1 + K_{2,2}P_2 + \ldots K_{2,n}P_n = \frac{dP_{c2}}{dt} \quad (T_2)$$

$$K_{n-1,1}P_1 + K_{n-1,2}P_2 + \ldots K_{n-1,n}P_n = \frac{dP_{c(n)}}{dt} \quad (T_{n-1})$$

$$P_1 + P_2 + \ldots P_n = P_{Total}$$

where $K_{1,n}$ is the permeation constant for gas species n in cell 1 at temperature $T_1$;

$K_{2,n}$ is the permeation constant for gas species n in cell 2 at temperature $T_2$;

$P_n$ is the partial pressure of gas species n on the high pressure side of the membrane.

$P_{c(n)}$ is the pressure within permeation cell of chamber n-1 and t is time.

5. Apparatus for receiving a sample gas and measuring the percentages of various known number (N) and kind of gas species present within said sample comprising:
   a plurality of chambers, each chamber configured to receive and combine sample gas;
   each chamber further including a discrete permeation cell having an internal volume isolated from the chamber by a permeable membrane;
   each chamber including a pressure sensor for measuring the pressure within the permeation cell resulting from gases permeating through said permeable membrane;
   means for evacuating the permeation cell;
   means for measuring the pressure build-up within the cell;
   said apparatus including a plurality of chambers including at least N chambers;
   means for maintaining each chamber at a discrete temperature, said temperature for each chamber different than the temperature for all other chambers.

6. The invention of claim 5 including a condenser having an outlet to each of said chambers, said condenser for stabilizing the water content of said samples.

7. The apparatus of claim 6 wherein each of said chambers has a membrane of the same permeation coefficient; and
   all said chambers are maintained at different discrete temperatures.

8. A process for receiving a gas sample and measuring the percentages of various known number (N) and kind of gas species present within said sample, comprising the steps of:
   providing at least (N-1) chambers, each provided chamber including a volume for isolating said sample gas and a permeation cell having an internal volume isolated from the rest of the chamber by a permeable membrane;
   maintaining each chamber at its own discrete temperature for a sufficient interval of time to thermally equilibrate the gas sample to the temperature of said chamber;
   evacuating the permeation cell of each said chamber;
   immediately after said evacuation step measuring the pressure buildup in said permeation cell for a sufficient interval of time during which a substantially linear permeation rate of gas across said membrane exists:
   measuring the total sample gas pressure in said chambers; and,
   determining from said measured pressures in said (N-1) cells the percentages of gases present by solving;

$$K_{1,1}P_1 + K_{1,2}P_2 + \ldots K_{1,n}P_n = P_{c1} \quad (T_1) \qquad (1)$$

$$K_{2,1}P_1 + K_{2,2}P_2 + \ldots K_{2,n}P_n = P_{c2} \quad (T_2)$$

$$K_{n-1,1}P_1 + K_{n-1,2}P_2 + \ldots K_{n-1,n}P_n = P_{c(n-1)} \quad (T_{n-1})$$

$$P_1 + P_2 + \ldots P_n = P_{Total}$$

where $K_{1,n}$ is the permeation constant for gas species n in cell 1 at temperature $T_1$;

$K_{2,n}$ is the permeation constant for gas species n in cell 2 at temperature $T_2$;

$P_n$ is the partial pressure of gas species n on the pressure side of the membrane;

$P_{c(n-1)}$ is the pressure within permeation cell of chamber n-1.

9. A process for receiving a gas sample and measuring the percentages of various known number (N) and kind of gas species present within said sample. comprising the steps of:
   providing at least (N) chambers, each provided chamber including a volume for isolating said sample gas and a permeation cell having an internal volume isolated from the rest of the chamber by a permeable membrane;
   maintaining each chamber at its own discrete temperature for a sufficient interval of time to thermally equilibrate the gas sample to the temperature of said chamber;
   evacuating the permeation cell of each said chamber;
   immediately after said evacuation step measuring the pressure buildup in said permeation cell for a sufficient interval of time during which a substantially linear permeation rate of gas across said membrane exists;
   measuring the total sample gas pressure in said chambers; and,
   determining from said measured pressures in said (N) cells the percentages of gases present by solving;

$$K_{1,1}P_1 + K_{1,2}P_2 + \ldots K_{1,n}P_n = P_{c1} \quad (T_1) \qquad (1)$$

$$K_{2,1}P_1 + K_{2,2}P_2 + \ldots K_{2,n}P_n = P_{c2} \quad (T_2)$$

$$K_{n-1,1}P_1 + K_{n-1,2}P_2 + \ldots K_{n-1,n}P_n = P_{c(n)} \quad (T_{n-1})$$

where $K_{1,n}$ is the permeation constant for gas species n in cell 1 at temperature $T_1$;

$K_{2,n}$ is the permeation constant for gas species n in cell 2 at temperature $T_2$;

$P_{c(n)}$ is the pressure within permeation cell of chamber n.

* * * * *